United States Patent
Howard et al.

(10) Patent No.: US 8,409,293 B1
(45) Date of Patent: Apr. 2, 2013

(54) KNEE PROSTHESIS

(75) Inventors: Michael J. Howard, Sammamish, WA (US); Kenneth D. Johannaber, Reno, NV (US)

(73) Assignee: Sevika Holding AG, Buonas (CH)

( * ) Notice: Subject to any disclaimer, the term of this patent is extended or adjusted under 35 U.S.C. 154(b) by 0 days.

(21) Appl. No.: 13/281,748

(22) Filed: Oct. 26, 2011

(51) Int. Cl.
*A61F 2/38* (2006.01)
(52) U.S. Cl. .................................. 623/20.15
(58) Field of Classification Search ..... 623/20.14–20.36
See application file for complete search history.

(56) References Cited

U.S. PATENT DOCUMENTS

| | | | |
|---|---|---|---|
| 4,213,209 A | 7/1980 | Insall et al. | |
| 4,634,444 A | 1/1987 | Noiles | |
| 4,888,021 A | 12/1989 | Forte et al. | |
| 5,330,533 A | 7/1994 | Walker | |
| 5,370,700 A | 12/1994 | Sarkisian et al. | |
| 5,413,604 A | 5/1995 | Hodge | |
| 5,725,584 A | 3/1998 | Walker et al. | |
| 6,458,160 B2 | 10/2002 | Biegun et al. | |
| 6,802,865 B2 | 10/2004 | Biegun et al. | |
| 7,160,330 B2 | 1/2007 | Axelson, Jr. et al. | |
| 7,261,740 B2 | 8/2007 | Tuttle et al. | |
| 7,326,252 B2 | 2/2008 | Otto et al. | |
| 7,497,874 B1 | 3/2009 | Metzger et al. | |
| 7,625,407 B2 | 12/2009 | Akizuki et al. | |
| 7,731,755 B2 | 6/2010 | Wyss et al. | |
| 7,837,737 B2 | 11/2010 | Hedley et al. | |
| 7,875,081 B2 | 1/2011 | Lipman et al. | |
| 2010/0191341 A1 | 7/2010 | Byrd | |

FOREIGN PATENT DOCUMENTS

EP    0 653 927    3/2001

OTHER PUBLICATIONS

Aesculap Orthopaedics's Catalog—e.motion, Knee endoprosthesis System by B/Braun.
Walker et al., Design Features of Total Knees for Achieving Normal Knee Motion Characteristics, The Journal of Arthroplasty vol. 24 No. 3 2009.

*Primary Examiner* — David Isabella
*Assistant Examiner* — Ann Schillinger
(74) *Attorney, Agent, or Firm* — Dorsey & Whitney LLP

(57) ABSTRACT

A knee prosthesis for use in a total knee replacement surgical procedure may include a femoral component, a tibial component and a meniscal component. Optionally, the prosthesis may also include a patellar component. The femoral component may include a bone attachment side and a joint facing side, the latter including an anterior joint surface, a posterior joint surface having a cross-sectional shape defining a portion of a cylinder, and medial and lateral grooves between the anterior and posterior joint surfaces. The meniscal component may include a number of features designed to mate with the femoral component to provide relatively natural movement and range of motion about the knee joint as well as stability and resistance to wear and tear.

19 Claims, 18 Drawing Sheets

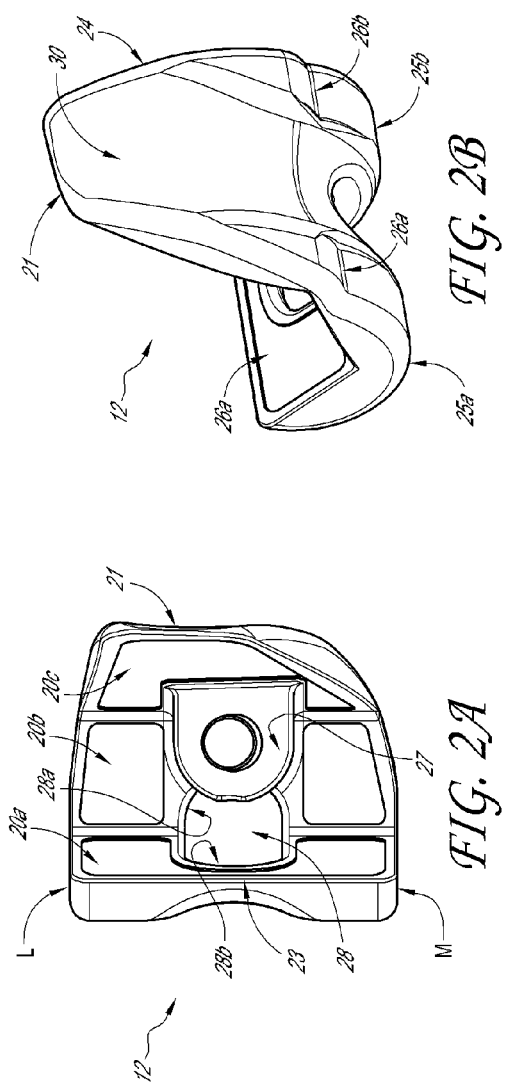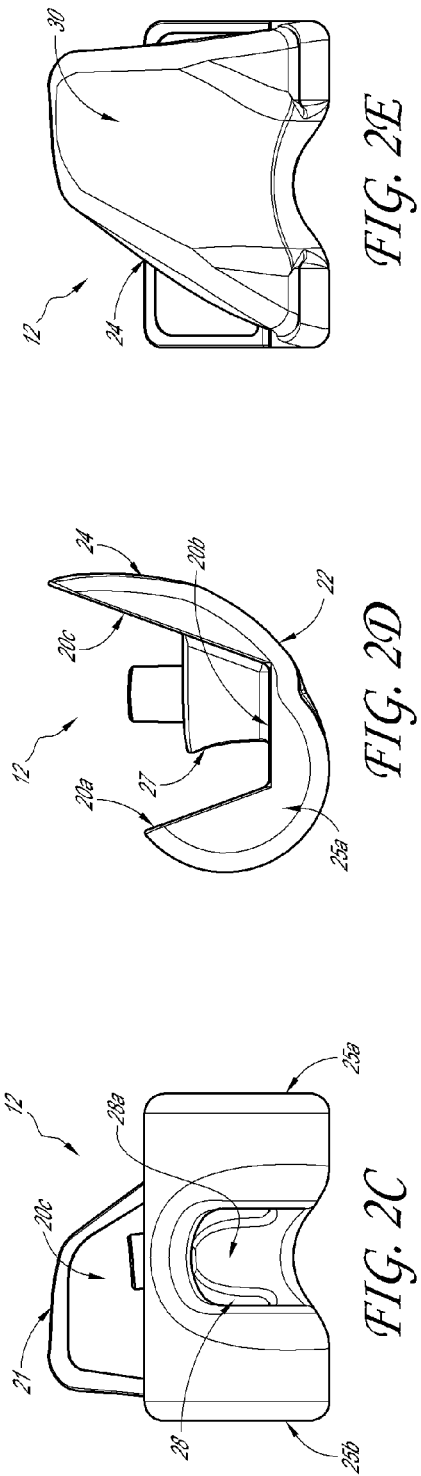

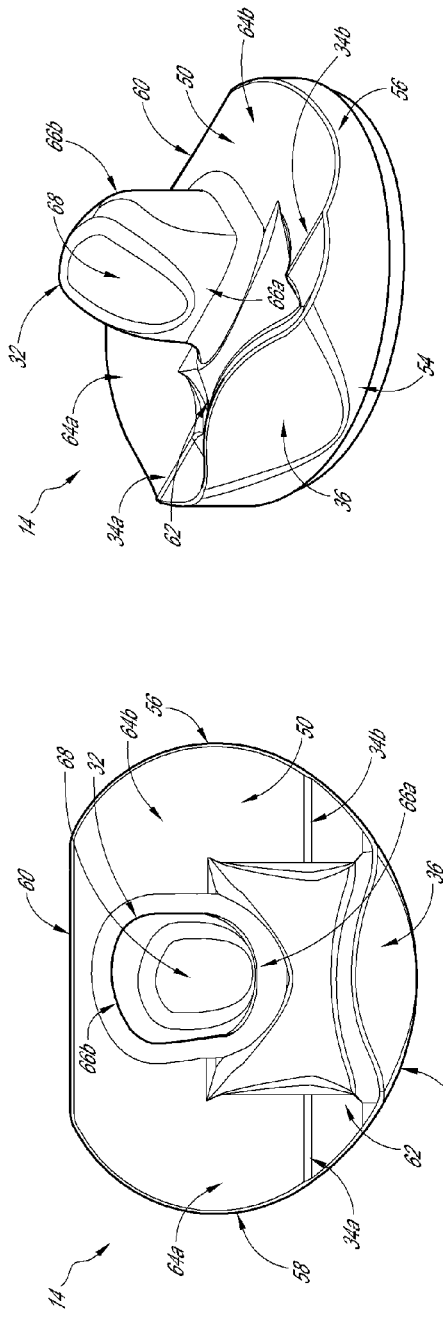
FIG. 3B
FIG. 3A
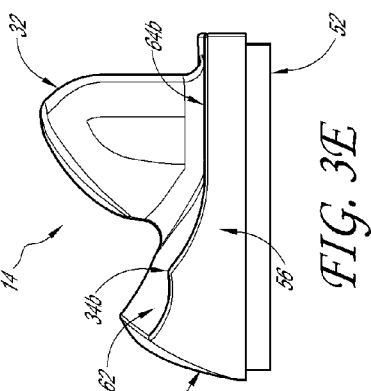
FIG. 3E
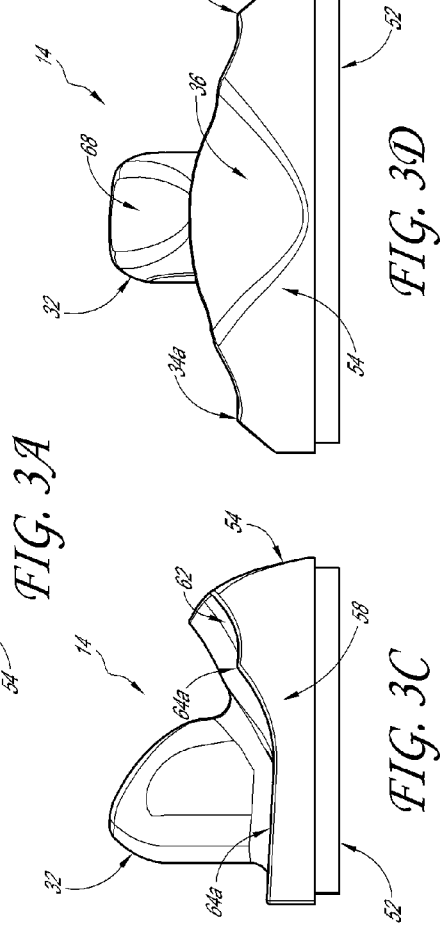
FIG. 3D
FIG. 3C

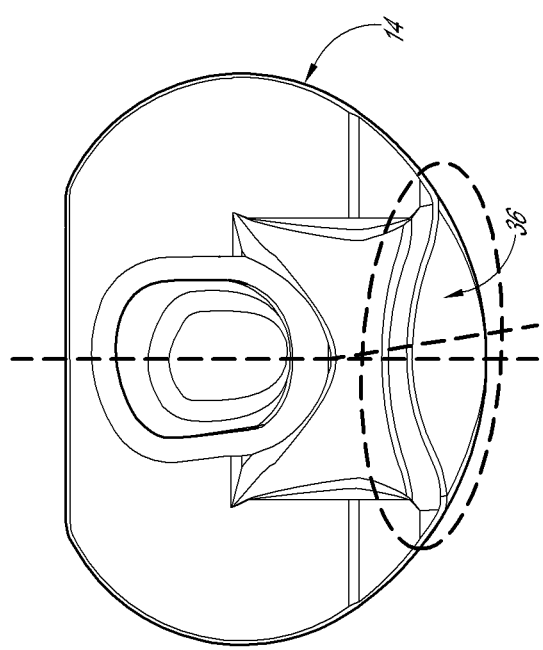

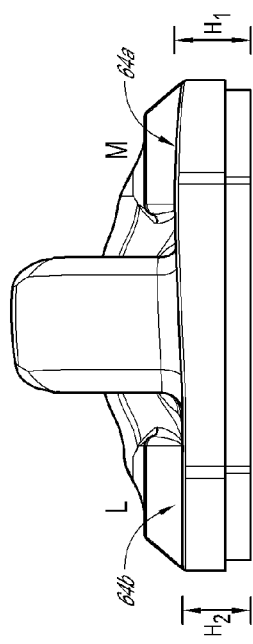
FIG. 3L
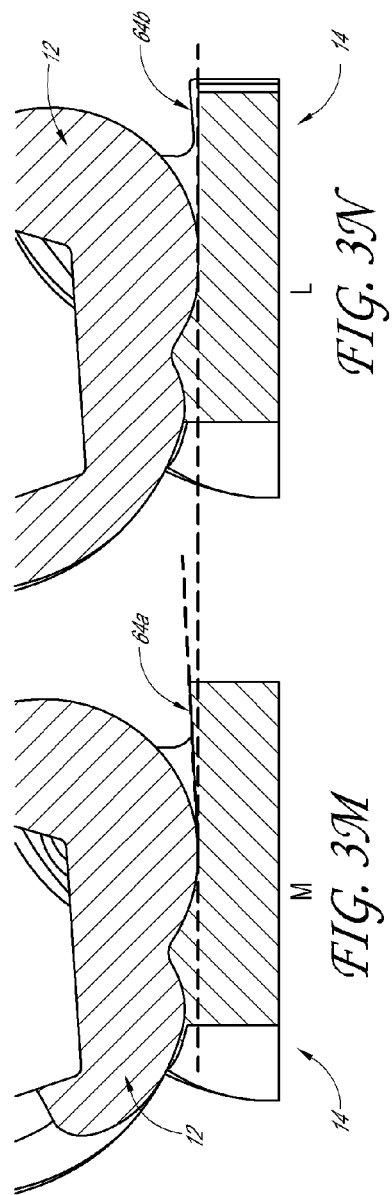
FIG. 3M
FIG. 3N

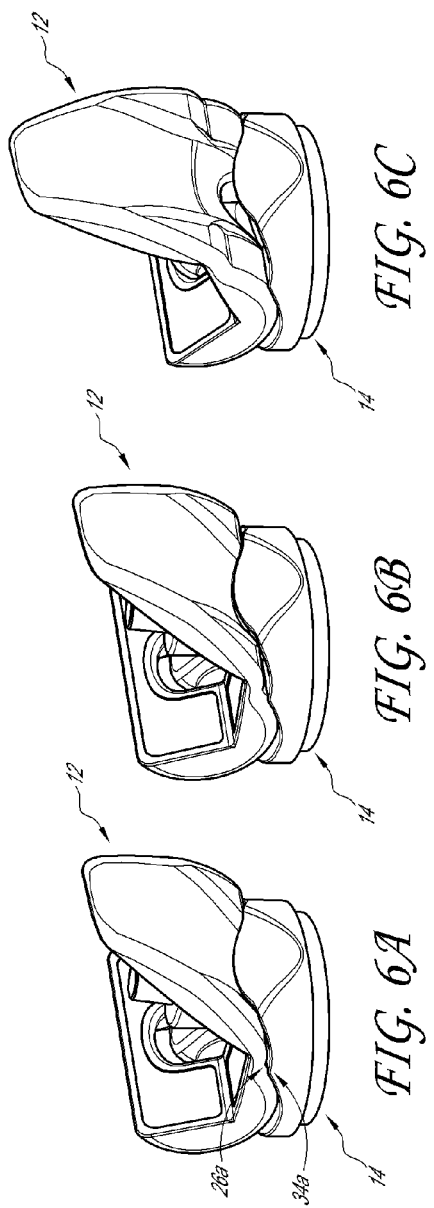
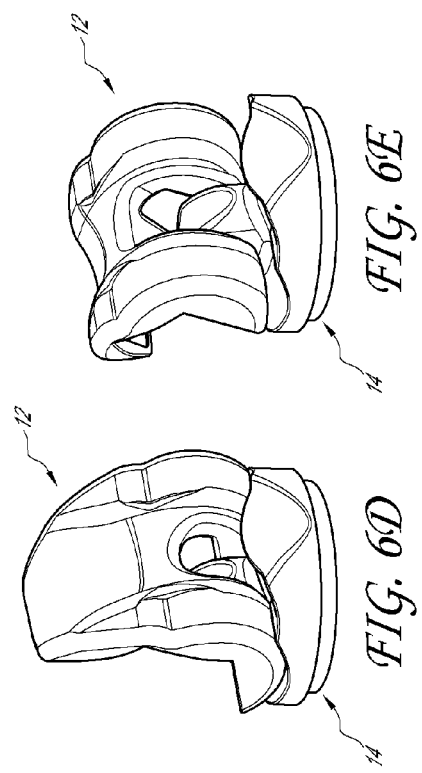
FIG. 6A
FIG. 6B
FIG. 6C
FIG. 6D
FIG. 6E

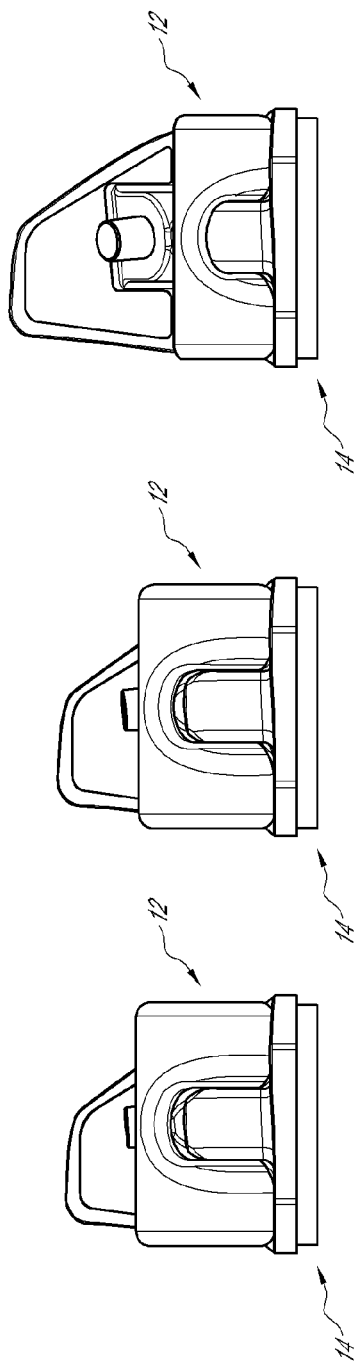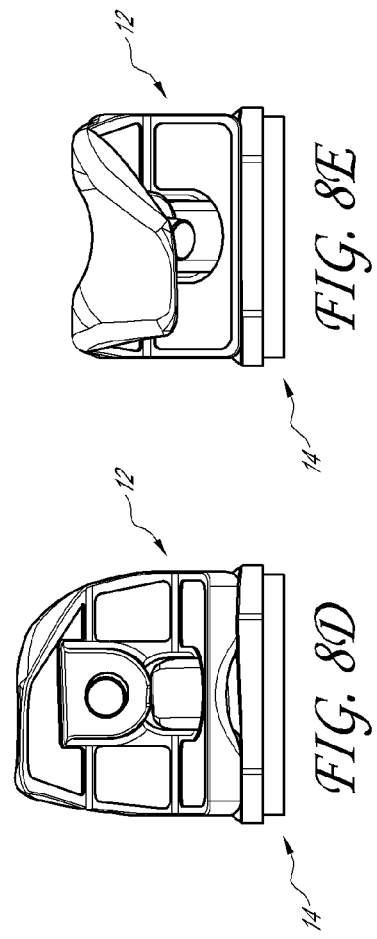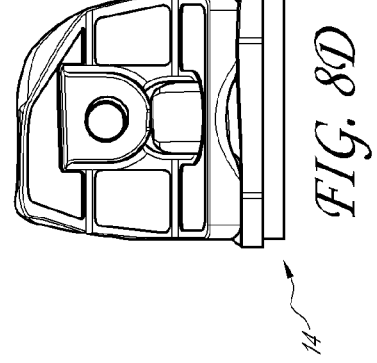

KNEE PROSTHESIS

BACKGROUND OF THE INVENTION

1. Field of the Invention

The invention is related to surgical devices for total knee replacement surgery. More specifically, the invention is related to a knee prosthesis for total knee replacement surgery.

2. Description of the Related Art

Approximately 581,000 total knee replacement surgeries (also referred to as total knee arthroplasty ("TKA")) are performed annually in the U.S. for the treatment of chronic knee pain and dysfunction. As the U.S. and world populations become older and more obese and knee joints endure greater wear and tear from increased loads and years of stress, TKA becomes a more and more commonly performed surgical procedure. The goals of TKA are to provide the patient with a knee joint that is pain free, moves naturally through a full range of motion, provides stability during motion and rest, and lasts as long as possible. Many different total knee implants (or "knee prostheses") have been developed in pursuit of these goals, but no total knee prosthesis is perfect. Some knee prostheses, for example, sacrifice some amount of stability in order to provide greater range of motion, while other prostheses do just the opposite. Other prostheses may provide certain kinematic advantages but may wear out more easily, thus requiring revision surgery more frequently. Although much of the success of TKA procedures can be attributed to surgeon skill and experience, rather than the prostheses themselves, improvements in total knee prostheses are still being sought.

The knee joint is generally defined as the point of articulation of the femur with the tibia. Structures that make up the knee include the distal femur, the proximal tibia, the patella, and the soft tissues within and surrounding the knee joint. Four ligaments are especially important in the functioning of the knee—the anterior cruciate ligament, the posterior cruciate ligament, the medial collateral ligament, and the lateral collateral ligament. In an arthritic knee, protective cartilage at the point of articulation of the femur with the tibia has been worn away, which causes significant pain and discomfort. In a TKA procedure, the distal end of the femur, the proximal end of the tibia, and often the inner surface of the patella are replaced with prosthetic parts to provide smooth, well-aligned surfaces for joint movement, while also creating a stable knee joint that moves through a wide range of motion.

A typical knee prosthesis includes a femoral component, a tibial tray or plateau and a tibial bearing insert (or "meniscal component") coupled to the tibial tray. The prosthesis may also include a patellar component, if replacing that bone surface is necessary. The femoral component generally includes a pair of laterally spaced apart condylar portions that have distal surfaces that articulate with complementary condylar elements formed in a tibial bearing insert.

As mentioned above, the TKA procedure and total knee prostheses generally try to achieve several basic goals: (1) Pain reduction/elimination; (2) Natural and full range of motion about the knee joint; (3) Joint stability; (4) Correctly sized and implanted joint to minimize wear and tear of the prosthesis; and (5) Preservation of as much of the patient's existing bone and soft tissue (ligaments and tendons) as possible. The goals of freedom of motion and stability can conflict with one another, since creating a more stable knee joint often means reducing freedom of motion. In trying to achieve these various goals, three categories of total knee prostheses/procedures have been developed.

In a knee joint resurfacing procedure, the articular surface of the distal femur and proximal tibia are "resurfaced" with respective condylar-type articular bearing components. These knee prostheses provide substantial rotational and translational freedom and require minimal bone resection to accommodate the components in the available joint space. The patellofemoral joint may also be resurfaced by a third prosthetic component. The femoral, tibial and patellar prosthetic resurfacing components are affixed to respective adjacent bone structure by a cementing or by a biological bone ingrowth fixation means or any other suitable technique.

In a second type of TKA, a mechanically linked or hinged knee prosthesis provides a fixed fulcrum flexion-extension capability. The hinged knee, therefore, is usually surgically indicated in selected cases where the surrounding soft tissue structures are grossly degenerated and incapable of providing functionally acceptable knee joint stability.

The third category of total knee prosthesis, the posterior stabilized total knee, provides more predictable kinematics than the first category. The posterior stabilized total knee prostheses essentially incorporate all of the functional features of the first category, that is, the resurfacing condylar-type of knee prostheses, in addition to incorporating a mechanical cam/follower mechanism for providing posterior (tibia-to-femur) constraint. The cam/follower mechanism is positioned within the intercondylar space of the femoral component and provides substitutional posterior constraint to compensate for lost anterior and/or posterior cruciate ligament function or for compromised posterior knee stability. This cam/follower mechanism enables the femur to roll back on the tibia, providing a mechanical advantage to the quadriceps during flexion.

Although many different posterior stabilized total knee prostheses have been developed and some work well, there is still much room for improvement. For example, most currently available prostheses compromise either knee joint stability or natural, full range of motion to an extent that is suboptimal for a patient. Additionally, most prostheses wear out more quickly than would be ideal, often in predictable wear patterns. Another limitation with conventional posterior cruciate substituting knee designs is that they require excess removal of bone for implantation. Excessive bone removal can lead to intraoperative fractures due to the stress concentration created by cutting out bone to accommodate the box of the design. Bone removal is also disadvantageous, because, in the event of revision surgery, the more bone available, the easier the revision surgery will be.

Therefore, a need exists for an improved knee prosthesis for a total knee arthroplasty procedure. Ideally, an improved prosthesis would provide natural kinematics, full range of motion through the knee joint, as well as a stable feeling joint. Also ideally, the knee prosthesis would have improved wear characteristics compared with most currently available prostheses. At least some of these objectives will be met by various embodiments of present invention.

SUMMARY OF THE INVENTION

The present invention provides an improved knee prosthesis for total knee arthroplasty. The prosthesis may have a number of advantages, such as but not limited to effectively replicating natural knee kinematics and reducing wear and tear of the prosthesis thus prolonging its useful life in situ. In various embodiments, the prosthesis may be provided as a system including multiple components, such as a femoral component, tibial component, meniscal component and patellar component, or some subset of those components.

In one aspect of the invention, a knee prosthesis for use in a total knee replacement surgical procedure may include a femoral component, a tibial component and a meniscal component. The femoral component may include a bone attachment side for attaching to a cut distal end of a femur and a joint facing side opposite the bone attachment side. The joint facing side of the femoral component may include: an anterior joint surface; a posterior joint surface having a cross-sectional shape defining a portion of a cylinder, wherein the posterior joint surface extends along at least 135 degrees of the cylinder and includes a lateral condyle, a medial condyle, and an intercondylar opening disposed between the lateral and medial condyles; and medial and lateral grooves extending across the femoral component between the anterior joint surface and the medial and lateral condyles. The tibial component may also include a bone attachment side for attaching to a cut proximal end of a tibia and a joint facing side opposite the bone attachment side.

The meniscal component may include an inferior side for mating with the tibial component, a superior side for mating with the femoral component, an anterior side, a posterior side, a lateral side and a medial side. The meniscal component may also include: an anterior articulating surface on the superior side for mating with the anterior joint surface of the femoral component; a posterior lateral articulating surface on the superior side for mating with the lateral condyle of the femoral component, the posterior lateral articulating surface having an approximately horizontal profile in an anterior-to-posterior direction; a posterior medial articulating surface on the superior side for mating with the medial condyle of the femoral component, the posterior medial articulating surface having an upward sloping profile in an anterior-to-posterior direction; medial and lateral projections on the superior side for mating with the medial and lateral grooves of the femoral component; a post extending from the superior surface and configured to mate with the intercondylar opening of the femoral component, wherein a central axis of the post is disposed closer to the posterior side than to the anterior side of the meniscal component; and an anterior cutout on the anterior side of the superior surface to prevent injury to a patellar tendon.

In one embodiment, the bone attachment side of the femoral component may include three surfaces for attaching to a three-cut configuration of the distal end of the femur. In one embodiment, the anterior joint surface of the femoral component may include a trochlear groove that is offset from a midline axis of the femoral component in a direction slanting from medial to lateral as the groove extends toward an anterior, superior edge of the femoral component. In one embodiment, the post of the meniscal component may have an asymmetrical shape in at least two dimensions. For example, in some embodiments, the post may have a helical twist shape as viewed from a superior aspect. Optionally, an anterior convex surface of the post may conform to an anterior concave surface of the intercondylar opening of the femoral component, and a posterior convex surface of the post may conform to a posterior concave surface of the intercondylar opening of the femoral component. Additionally, in some embodiments a posterior portion of the post may be wider than an anterior portion of the post. Also optionally, a superior surface of the post may slope downward in a posterior-to-anterior direction, and the superior surface may have an asymmetric convex configuration.

In some embodiments, the anterior cutout on the meniscal component may be asymmetrically disposed along the anterior side, biased toward the lateral side. Also in some embodiments, the prosthesis may further include a patellar component having a cutout portion on an inferior edge.

In another aspect of the invention, a meniscal component of a knee prosthesis for use in a total knee replacement surgical procedure may include: an inferior side for mating with a tibial component of a knee prosthesis; a superior side for mating with a femoral component of the knee prosthesis; an anterior side, a posterior side, a lateral side and a medial side; a concave anterior articulating surface on the superior side toward the anterior side for mating with a convex anterior joint surface of a femoral component; a posterior lateral articulating surface on the superior side for mating with a lateral condyle of the femoral component, the posterior lateral articulating surface having an approximately horizontal profile in an anterior-to-posterior direction; a posterior medial articulating surface on the superior side for mating with a medial condyle of the femoral component, the posterior medial articulating surface having an upward sloping profile in an anterior-to-posterior direction; medial and lateral projections on the superior side for mating with medial and lateral grooves on the femoral component; a post extending from the superior surface and configured to mate with the intercondylar opening of the femoral component, wherein a central axis of the post is disposed closer to the posterior side than to the anterior side of the meniscal component; and an anterior cutout on the anterior side of the superior surface to prevent injury to a patellar tendon. As described above, the post of the meniscal component may have an asymmetrical shape in at least two dimensions.

In another aspect of the present invention, a knee prosthesis for use in a total knee replacement surgical procedure may include a femoral component as described above and a meniscal component. The meniscal component may be largely as describe above but may include a bone attachment side for attaching to a cut proximal end of a tibia and a superior side for mating with the femoral component, thus eliminating the need for a separate tibial component. In some embodiments, the meniscal component may be made entirely of a polymer such as ultra-high-molecular-weight polyethylene (UHMWPE). As in previously described embodiments, the prosthesis may optionally also include a patellar component having a cutout portion on an inferior edge.

For a further understanding of the nature and advantages of the invention, reference should be made to the following description taken in conjunction with the accompanying figures. However, each of the figures is provided for the purpose of illustration and description only and is not intended to limit the scope of the embodiments of the present invention.

BRIEF DESCRIPTION OF THE DRAWINGS

FIGS. 2A-2E are top, perspective, posterior, medial and anterior views, respectively, of a femoral component of a knee prosthesis, according to one embodiment;

FIGS. 3A-3E are top, perspective, medial, anterior and lateral views, respectively, of a meniscal component of a knee prosthesis, according to one embodiment;

FIG. 3K is a top view of a meniscal component of a knee prosthesis, according to one embodiment;

FIGS. 3L-3N are posterior, medial and lateral views, respectively, of a meniscal component of a knee prosthesis, according to one embodiment;

FIGS. 6A-6E are perspective views of femoral and meniscal components of a knee prosthesis, according to one embodiment, demonstrating how the components move during a range of motion of a knee joint from extension to flexion as follows: 4 degrees hyperextension (FIG. 6A); 0 degrees flexion (FIG. 6B); 45 degrees flexion (FIG. 6C); 90 degrees flexion (FIG. 6D); and 135 degrees flexion (FIG. 6E);

FIGS. 8A-8E are posterior views of the femoral and meniscal components through the same range of motion shown in FIGS. 6A-6E and 7A-7E.

DETAILED DESCRIPTION OF THE PREFERRED EMBODIMENT

Figure 1A:
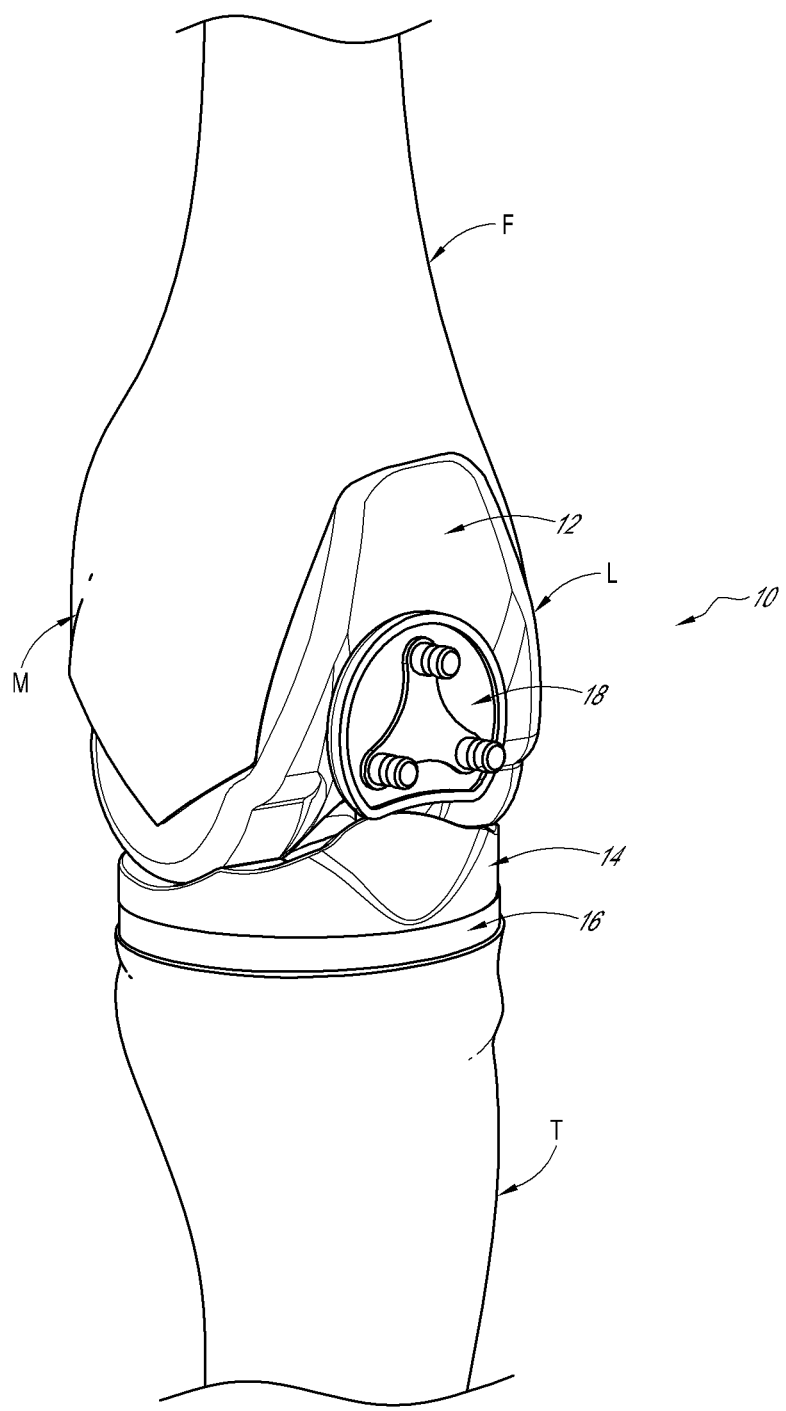
FIG. 1A is a perspective view of a knee prosthesis, including femoral, meniscal, tibial and patellar components, in place within a knee joint, according to one embodiment.

Referring to FIGS. 1A-1D, in one embodiment, a knee prosthesis system 10 may include a femoral component 12, a meniscal component 14, a tibial component 16, and optionally a patellar component 18. In FIG. 1A, knee prosthesis system 10 is shown with patellar component 18, while in FIGS. 1B-1D, it is shown without patellar component 18. In other embodiments, system 10 may be provided without tibial component 16, for example when meniscal component 14 attaches directly to the cut tibia (not shown). In yet other embodiments, multiple sizes of one or more components may be provided as part of system 10, for example as a kit or suite of operating room tools so that a surgeon can select a desired size of each component or set of components. Generally, therefore, system 10 may include any two or more components of a knee prosthesis as described herein. Although system 10 is typically described below as including femoral 12, meniscal 14 and tibial 16 components, with an optional patellar component 18, this description is provided for exemplary purposes and should not be interpreted to limit the scope of the claims.

FIG. 1A shows knee prosthesis system 10 in place within a knee joint of a left leg. Here, femoral component 12 is attached to the femur F, tibial component 16 is attached to the tibia T, meniscal component 14 is disposed between the two, and patellar component is floating in a position generally located where it would be when attached to a patella (not shown for ease of illustration). The ligaments or tendons of the knee joint are not shown in FIG. 1, so that system 10 may be more easily seen.

The embodiment of system 10 and components 12, 14, 16, 18 shown in FIG. 1A and many of the subsequent figures in this application is configured for a left knee. It is described as having a lateral side L and a medial side M, conforming to the lateral and medial sides of the knee, respectively. Of course, in another embodiment, system 10 is provided in mirror image for use on a right knee, and in some embodiments a kit or system may include multiple knee prostheses for a left knee and a right knee or even for multiple sizes of left and right knees. Therefore, although many references will be made to the lateral side L and medial side M of components 12, 14, 16, 18 and system 10, these sides may be reversed in alternative embodiments, and the descriptions thus should not be interpreted as limiting the invention as claimed.

Figure 1B:
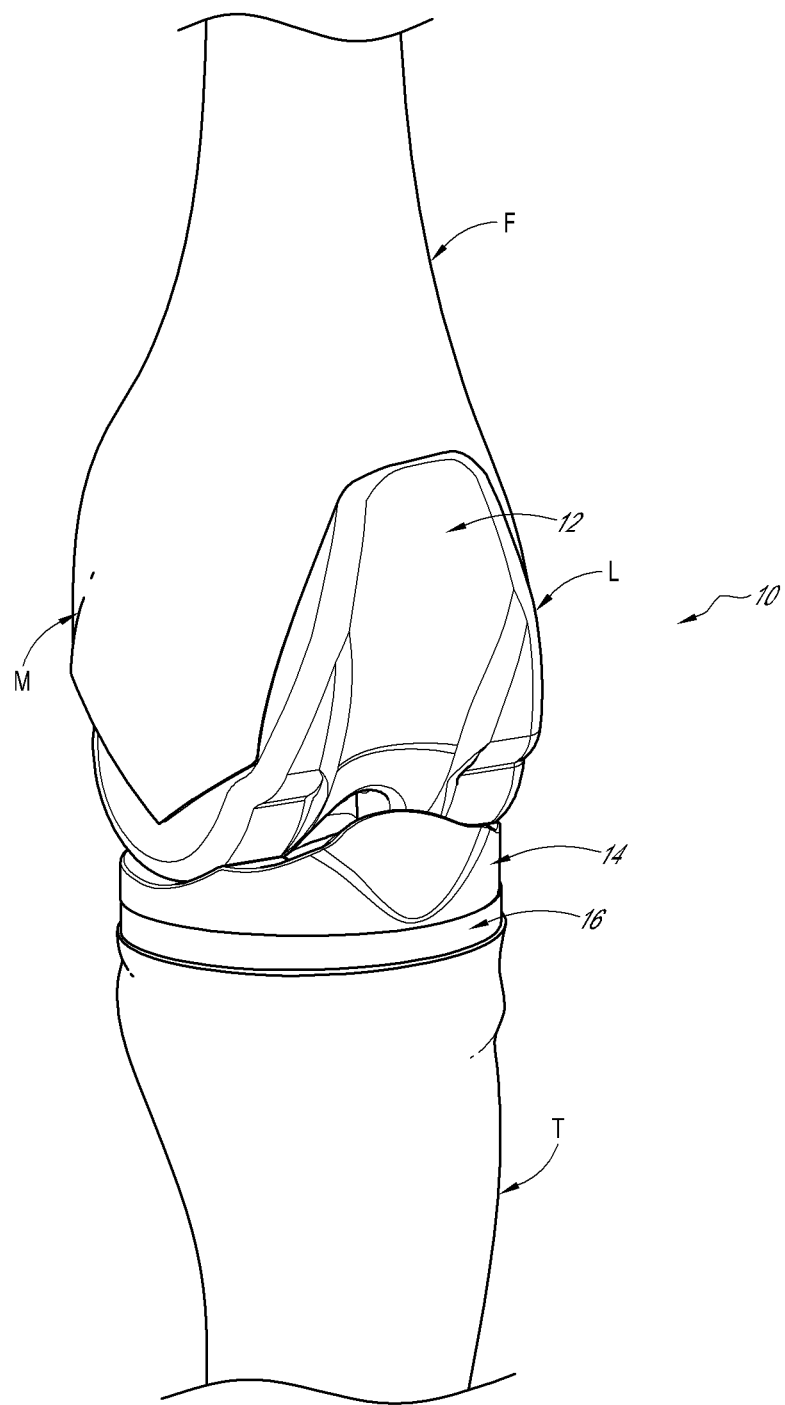
FIG. 1B is a perspective view of the knee prosthesis of FIG. 1A, with the patellar component removed.
Figure 1C:
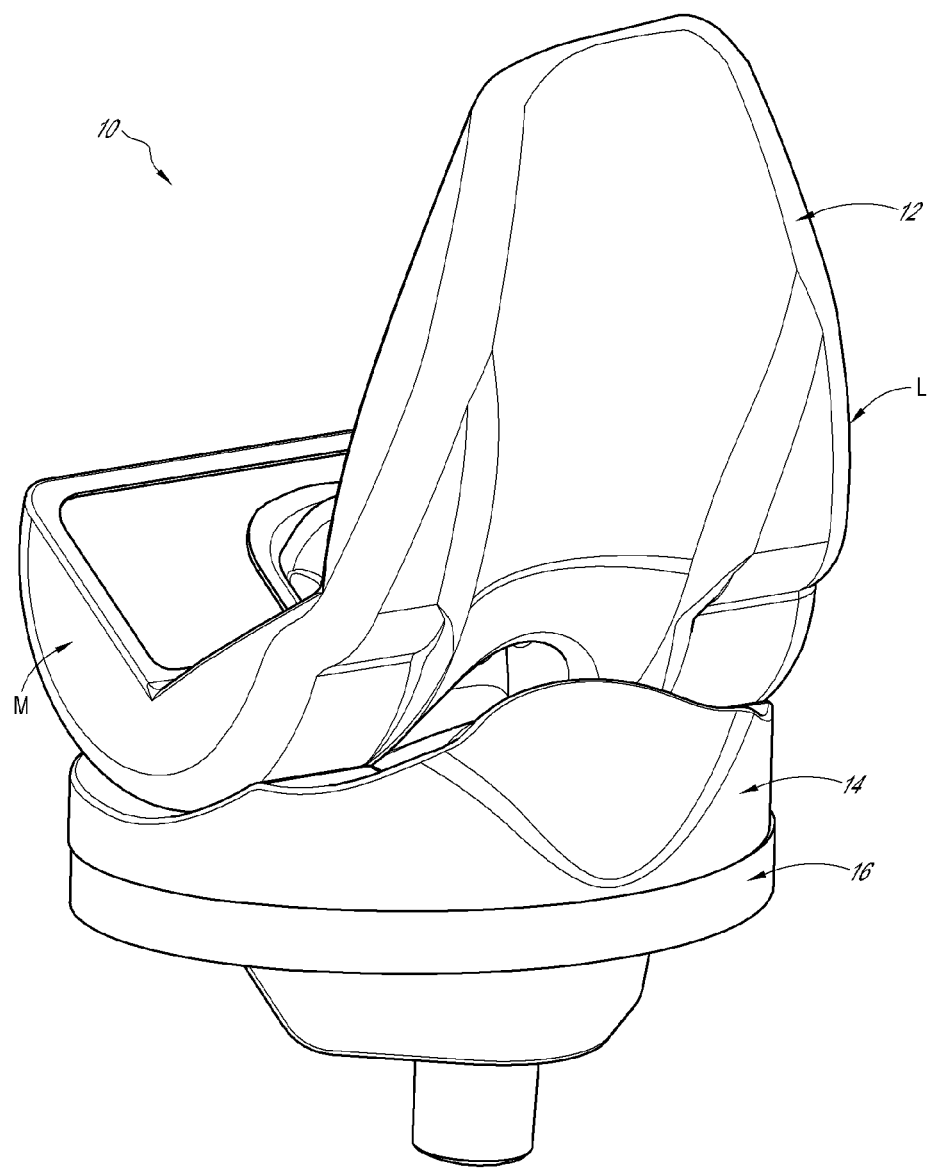
FIG. 1C is a perspective view of the knee prosthesis of FIGS. 1A and 1B without the femur or tibia shown.

FIG. 1B illustrates knee prosthesis system 10 in place within a knee joint with patellar component 18 removed. FIG. 1C is a perspective view of knee prosthesis system 10 by itself, also without patellar component 18.

Figure 1D:
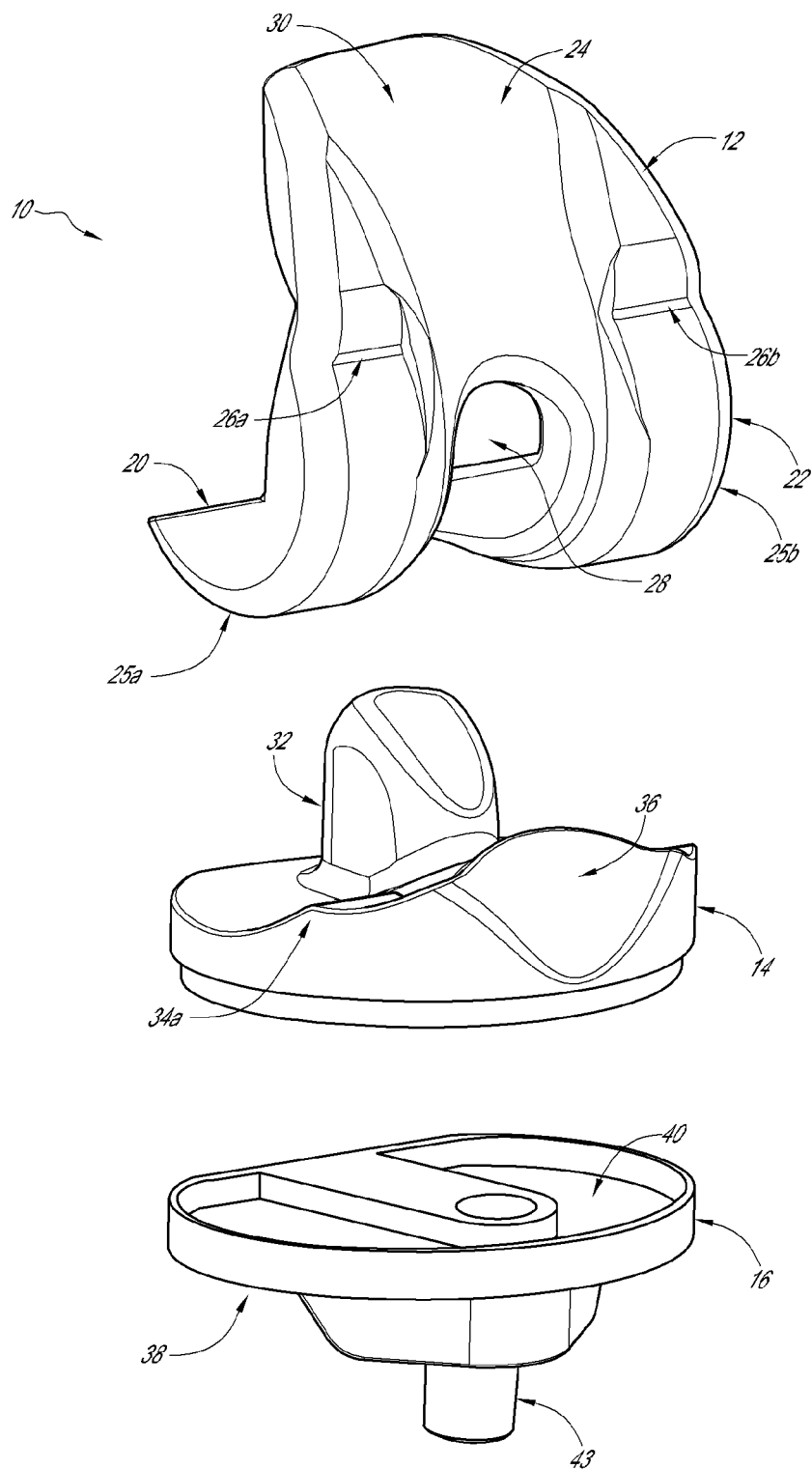
FIG. 1D is an exploded view of the knee prosthesis of FIGS. 1A-1C.

Referring now to FIG. 1D, an exploded view of knee prosthesis system 10 helps illustrate further details of femoral component 12, meniscal component 14 and tibial component 16. For example, in the embodiment shown, femoral component 12 includes a bone attachment side 20 and a joint facing side 22. Bone attachment side 20 has three surfaces at different angled orientations from one another (see FIGS. 2A-2D), to provide for attachment to a 3-cut distal end of a femur F. In an alternative embodiment, bone attachment side 20 may include five surfaces, for attachment to a 5-cut distal end of a femur F, or any other suitable number of surfaces to provide for alternative femoral bone cut configurations. Generally, the 3-cut configuration is used for revision TKA procedures, while the 5-cut configuration is used for original (or "primary") TKA procedures. This is not a requirement for the present application, however, and although the 3-cut bone attachment side 20 is shown and described herein, system 10 may be used for primary or revision TKA procedures in various embodiments.

Joint facing side 22 of femoral component 12 may include an anterior articulating surface 24, a posterior articulating surface 25 including a medial condyle 25a and a lateral condyle 25b, a medial groove 26a and a lateral groove 26b between the articulating surfaces 24, 25, an intercondylar opening 28, and a trochlear groove 30 extending vertically along anterior articulating surface 24. These and other features of femoral component 12 are described in greater detail below.

Still referring to FIG. 1D, meniscal component 14 may include a post 32 for mating with the intercondylar opening 28 of femoral component 12, a medial projection 34a and a lateral projection 34b (not visible in this figure) for mating with lateral grooves 26a, 26b of femoral component 12, and an anterior cutout 36 on its anterior/superior side for preventing injury to the patellar tendon. These and other features of meniscal component 14 are described in greater detail below.

Tibial component 16 includes a joint facing side 40, a bone attachment side 38, and a bone attachment stem 43 for extending into the tibia to facilitate bone attachment. Tibial component 16 is also described in greater detail below.

All components 12, 14, 16, 18 of knee prosthesis system 10 may be made of any suitable material for manufacturing knee prostheses. For example, in some embodiments, femoral component 12 and tibial component 16 may be made of a metal, while meniscal component 14 and patellar component 18 may be made of a polymer. In other embodiments, tibial component 16 may also be made of a polymer. In some embodiments, one of more of the components may be made of ceramic. Knee prosthesis system 10, therefore, may incorporate any suitable material(s) and combinations thereof. Typical implant metals include CoCr (Cobalt-Chrome), and Ti-6Al-4V (Titanium Alloy). A typical polymer is UHMWPE (Ultra-High Molecular Weight Polyethylene). Ceramics include Zirconia, Zirconia-Toughened Alumina (ZTA), Alumina, and oxidized zirconium (metal-ceramic). Some implants may also be coated (or part of an implant may be coated) with any of a number of suitable coating materials. For example, some coatings are used on implants to increase bone-cement-implant adhesion and promote ingrowth. Potential coatings include HA (Hydroxyapatite), TPS (Titanium Plasma Spray), RBM (Resorbable blast media) and porous coatings (spherical beads, asymmetrical powder and irregular particle coatings).

Components 12, 14, 16, 18 of knee prosthesis system 10 may also be provided in any suitable size, combinations of sizes, kits including multiple sizes, or the like. For example, in one embodiment, femoral component 12 may have any of a number of different distal thicknesses (or "heights") while maintaining the distal profile, posterior thickness and anterior thickness of joint facing surface 22. These femoral components 12 of multiple thicknesses may be provided to allow a surgeon to select a desired thickness without needing to use augments or offsets. One example of such a kit of different distal thicknesses of a femoral component is described in U.S. Pat. No. 7,837,737, the disclosure of which is hereby incorporated by reference. Thus, knee prosthesis system 10 is not dependent on sizes of components and may be provided in any suitable size or combination of sizes as desired.

FIGS. 2A-2E show femoral component 12 in greater detail. FIG. 2A, a top view, shows the three surfaces 20a, 20b and 20c of this embodiment of bone attachment side 20, a bone attachment member 27, an anterior/superior edge 21, a posterior/superior edge 23, and intercondylar opening 28, which has an anterior surface 28a and a posterior surface 28b. This view also shows that anterior joint surface 24 is asymmetric, slanting toward the lateral side L toward the anterior/superior edge 21. Bone attachment member 27 may have any of a number of suitable configurations and may include a post, as shown. Ideally, bone attachment member 27 is made as small as possible while also helping provide secure attachment to the femur, so that as small a femoral cut as possible may be made.

The shape and location of intercondylar opening 28 and its anterior 28a and posterior 28b surfaces are configured for mating with post 32 on meniscal member 14. Surfaces 28a, 28b may be regarded as cam surfaces, which interact with corresponding anterior and posterior surfaces of post 32 during rotation of the knee joint. Posterior cam surface 28b produces rollback in the form of posterior translation of the femur relative to the tibia as it rides against meniscal component post 32. Anterior cam surface 28a is used to stabilize femoral component 12 with meniscal component 14 in full extension.

Shape of intercondylar opening 28 is designed to conform closely to the shape of post 32, so that the two parts conform to one another during movement to enhance stability while still allowing for a full range of motion.

Referring now to FIG. 2B, a perspective view of femoral component 12, trochlear groove 30 on anterior surface 24 is shown in greater detail, as are medial groove 26a and lateral groove 26b. The asymmetry of anterior surface 24 is also demonstrated in this figure. As mentioned above, anterior articulating surface 24 of femoral component 12 is asymmetrically slanted toward the lateral side of femoral component 12 toward its anterior/superior edge 21. Trochlear groove 30 is also offset laterally. In other words, instead of traveling vertically up anterior articulating surface 24, trochlear groove 30 angles toward the lateral side in the anterior/superior direction. This offset configuration of trochlear groove 30 improves patellar tracking.

Medial and lateral grooves 26a, 26b divide femoral component 12 into anterior and posterior articulating surfaces 24, 25, the latter having two parts—medial condyle 25a and lateral condyle 25b. Together with protrusions 34a, 34b of meniscal component 14, grooves 26a, 26b help provide knee prosthesis 10 with anterior-posterior stability, help reduce paradoxical shift/translation of the knee, and enhance patellofemoral tracking when implanted in a knee joint.

FIG. 2C is a posterior view of femoral component 12. From this viewpoint, intercondylar opening 28 and its anterior surface 28a are visible. Also, the cylindrical shape of posterior articulating surface 25 is evident. This cylindrical shape is discussed further below, and an alternative embodiment is discussed in relation to FIG. 3A.

Figure 2G:
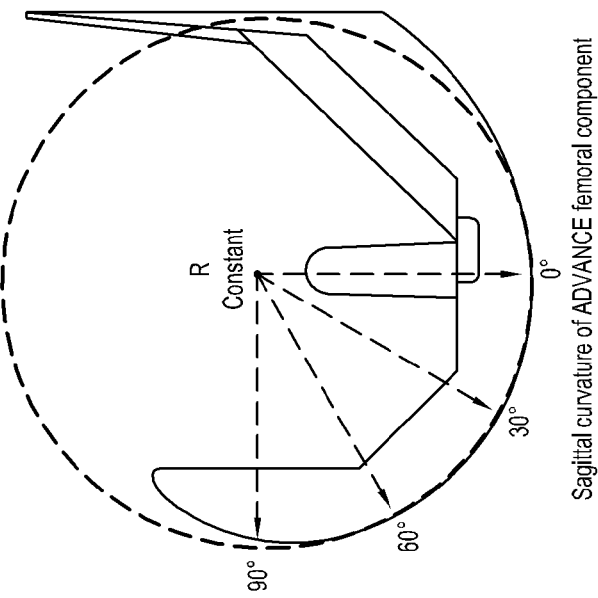
FIG. 2G is a side view of a prior art femoral component of a knee prosthesis.
Figure 2F:
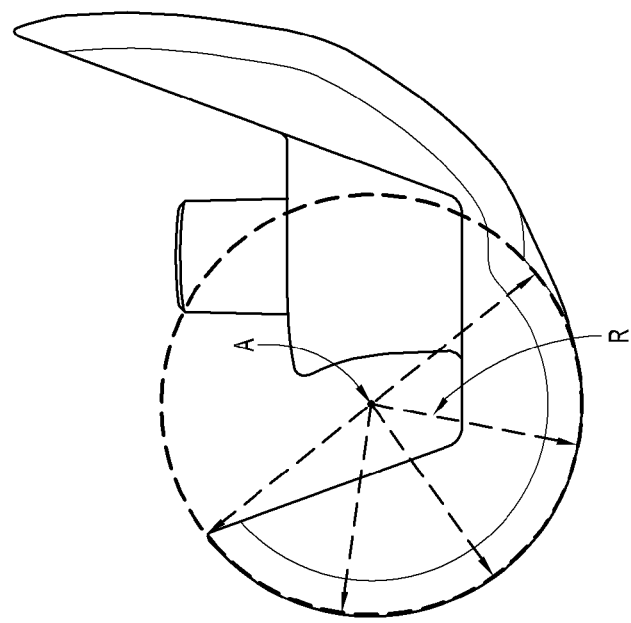
FIG. 2F is a side, diagrammatic view of a femoral component, according to one embodiment.
Figure 2J:
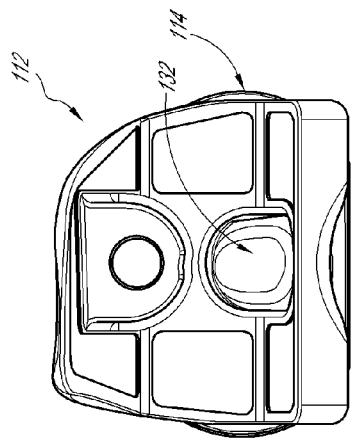
FIGS. 2H-2K are posterior comparison views of two femoral components, according to two different embodiments.
Figure 2K:
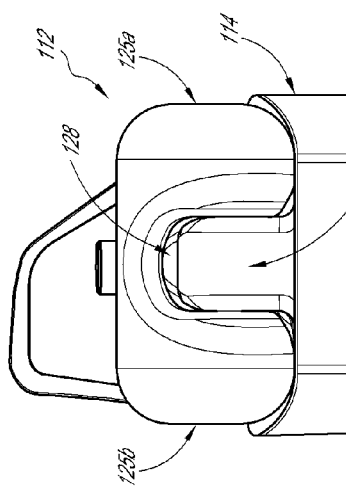

In FIGS. 2D and 2F, medial side views, the cylindrical shape of posterior articulating surface 25 is again shown. As the knee rotates through its range of motion from extension to flexion and back to extension, the tibia rotates about the femur around an axis of rotation A (FIG. 2F). Posterior articulating surface 25, including medial condyle 25a and lateral condyle 25b, are the portion of femoral component 12 about which the majority of this rotation occurs. Posterior articulating surface 25 may thus be said to have an axis of rotation A about which the cylindrical shape of surface 25 is formed. This cylinder may be said to have a radius R from axis A to posterior surface 25, One of the advantageous features of femoral component 12 is that posterior joint surface 25 conforms to the radius R of the cylinder drawn about the axis of rotation A for at least about 120 degrees, and more preferably at least about 135 degrees, and even more preferably about 180 degrees or more. This configuration of posterior articulating surface 25 may be referred to as a "cylindrical radius," which ends in grooves 26a, 26b. By contrast, and referring to FIG. 2G, currently available femoral components of knee prosthesis generally have a posterior portion that conforms to the radius of a cylinder for only 90 degrees at most. The posterior shapes of these currently available devices then move away from the radius. The advantage of having posterior surface 25 that conforms to the radius of the cylinder for at least 120 degrees (and preferably closer to or equal to 180 degrees) is that, along with grooves 26a, 26b, this feature enhances stability and the natural kinematics (motion) of the knee. Tests have shown that this shape provides a more natural knee movement.

Still referring to FIGS. 2D and 2F, femoral component 12 may also be described as having an anterior radius of curvature involving anterior articulating surface 24 and a posterior radius of curvature R involving posterior articulating surface 25. Posterior radius of curvature R was just described and involves the tibiofemoral portion of the knee joint. The anterior radius of curvature refers to the radius of rotation of the patella about the femur (or femoral component 12)—i.e., the patellofemoral joint. The anterior and posterior curvatures intersect at the location of grooves 26a and 26b.

FIG. 2E is an anterior/superior view of femoral component 12, again demonstrating the asymmetrical shape of anterior articulating surface 24 and trochlear groove 30. As mentioned previously, this asymmetry is reversed in a knee prosthesis configured for the opposite (right) knee.

Figure 2H:
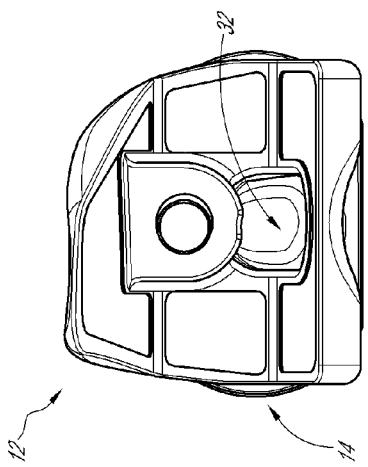
Figure 2I:
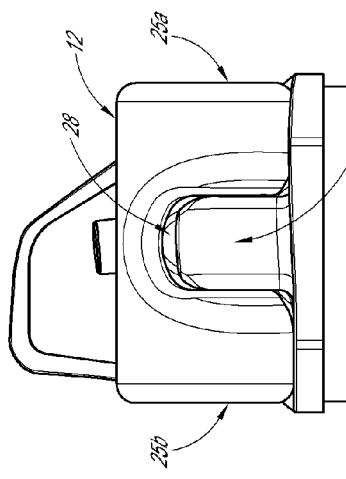

Referring now to FIGS. 2H and 2I, an alternative embodiment of femoral component 12 is explained. FIG. 2H is a posterior view of the previously described embodiment of femoral component 12 and meniscal component 14 with post 32. Femoral component 12 has medial 25a and lateral 25b condyles, which have a generally cylindrical overall shape, and intercondylar opening 28 between the two. In an alternative embodiment, however, as shown in FIG. 2I, a femoral component 112 may have an intercondylar opening 128 and a medial condyle 125a and a lateral condyle 125b that conform to more of a spherical shape. In this embodiment, meniscal component 114 also has a more concave shape to mate with the spherical shape of femoral component 112. In alternative embodiments, either of these configurations of femoral component 12, 112 and meniscal component 14, 114 may be used.

Referring now to FIGS. 3A-3E, meniscal component 14 is shown in greater detail. Meniscal component 14 may be described as having a superior side 50 for mating with femoral component 12, an inferior side 52 for mating with tibial component 16, an anterior side 54, a lateral side 56, a medial side 58 and a posterior side 60. On superior side 50, as mentioned previously, meniscal component 14 includes posterior stabilization post 32, medial protrusion 34a for mating with medial groove 26a of femoral component, lateral protrusion 34b for mating with lateral groove 26b of femoral component, and anterior cutout 36 for preventing injury to a patellar tendon. Superior side 50 may also include an anterior articulating surface 62 for mating with anterior joint surface 24 of femoral component 12, a posterior medial articulating surface 64a for mating with medial condyle 25a of femoral component 12, and a posterior lateral articulating surface 64b for mating with lateral condyle 25b of femoral component 12.

As shown in FIG. 3A (a top view of meniscal component 14), post 32 may be described as having an anterior surface 66a and a posterior surface 66b. These surfaces 66a, 66b interact with anterior cam surface 28a and posterior cam surface 28b of intercondylar opening 28 of femoral component 12. Compared to currently available knee prostheses, post 32 is located farther toward posterior side 60 of meniscal component 14. For example, a central axis drawn vertically through approximately the center of post 32 is located closer to posterior side 60 than to anterior side 54. In one embodiment, post 32 is located approximately one third of the total anterior/posterior distance from posterior side 60. The advantages of this more posterior location of post 32 may include: (1) It better replicates natural knee motion/kinematics by allowing for greater rollback of the tibia over the femur; (2) By placing the post more posterior, and having a cylindrical radius with a center that is close to the insertion point of the PCL, this design engages the posterior stabilizer earlier and transitions easily from rotation to posterior "rollback" at the correct time to replicate natural kinematics; (3) It makes posterior surface 66b of post 32 engage with posterior cam surface 28b of femoral component 12 earlier in flexion (i.e., at a smaller angle of flexion, such as about 20 degrees instead of about 45 degrees with conventional prostheses), which increases stability; (4) It increases the range of motion about the knee; and (5) It allows less bone removal from the distal femur during the surgical procedure.

Figure 3G:
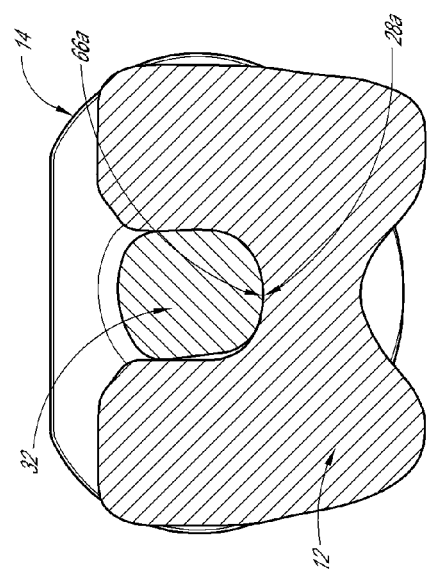
FIG. 3G is a top, cross-sectional view of meniscal and femoral components of a knee prosthesis, showing conforming anterior surfaces, according to one embodiment.
Figure 3F:
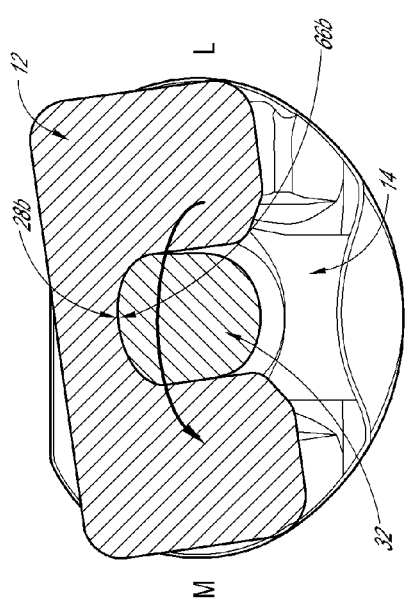
FIG. 3F is a top, cross-sectional view of meniscal and femoral components of a knee prosthesis, showing conforming posterior surfaces according to one embodiment.

Referring now to FIGS. 3A and 3F, in at least one embodiment, posterior stabilization post 32 has a shape that conforms in multiple different ways to intercondylar opening 28 of femoral component 12. Post 32 is also asymmetrical in multiple ways. For example, as illustrated by FIGS. 3A and 3F, post 32 may have a slight helical twist from a top down view (in a counterclockwise direction in the figure). The helical twist shape may allow posterior cam surface 28b of femoral component 12 to better conform to posterior surface 66b of post during the range of motion of the knee and especially during internal tibial rotation, which may reduce wear and tear on post 32. The twist shape may also help facilitate natural knee kinematics by encouraging posterior translation of lateral condyle 25b and pivoting of medial condyle 25a during flexion (illustrated by curved arrow in FIG. 3F).

With reference to FIGS. 3A and 3G, anterior surface 66a of post 32 may also have a shape that conforms to anterior cam surface 28a of intercondylar opening 28. This conformity of the corresponding surfaces helps stabilize the knee when returning from flexion to extension or when simply in a state of extension or low flexion. The conformity of the surfaces also reduces peak stresses on anterior cam surface 66a, reducing potential for wear and premature fatigue.

Figure 3H:
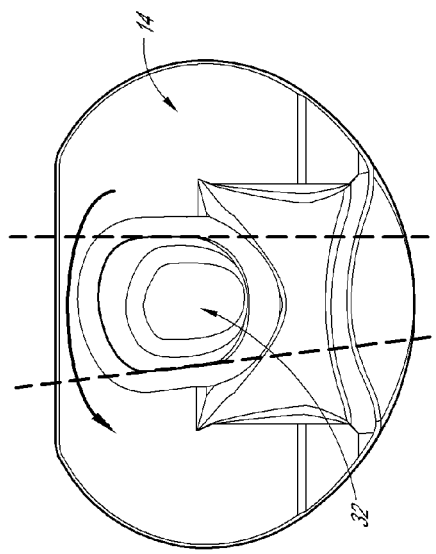
FIG. 3H is a top view of a meniscal component of a knee prosthesis, according to one embodiment.

Referring to FIGS. 3A and 3H, post 32 may also have a tapered profile, looking from a top down view, going from a wider profile posteriorly to a narrower profile anteriorly. This tapered profile may be produced by making an angular cut down the medial side of post 32, thus creating another asymmetry. Again, this asymmetry helps facilitate internal tibial rotation during flexion of the knee. The tapered profile maintains prosthesis constraint/stability between post 32 and intercondylar opening 28 in early flexion and extension, while allowing internal tibial rotation at higher flexion angles in the kinematic range of motion.

Figure 3J:
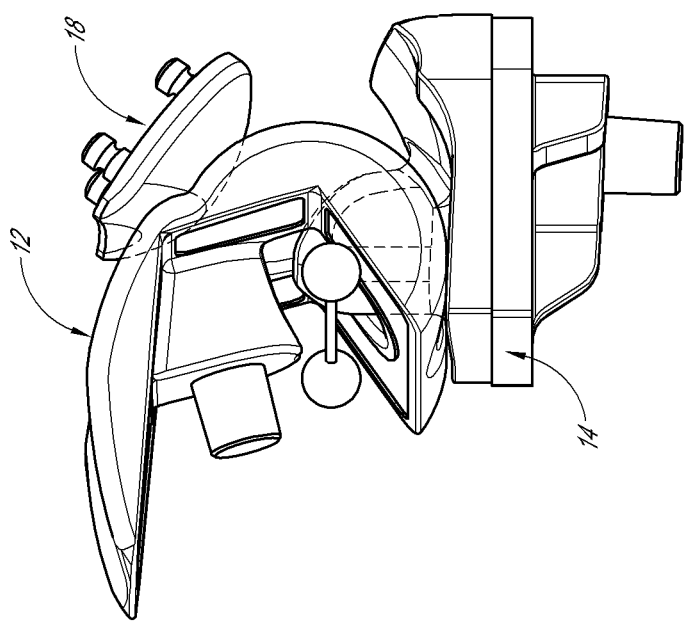
FIGS. 3I and 3J are a top view of a meniscal component and a side view of meniscal, femoral and patellar components of a knee prosthesis, respectively, according to one embodiment.
Figure 3I:
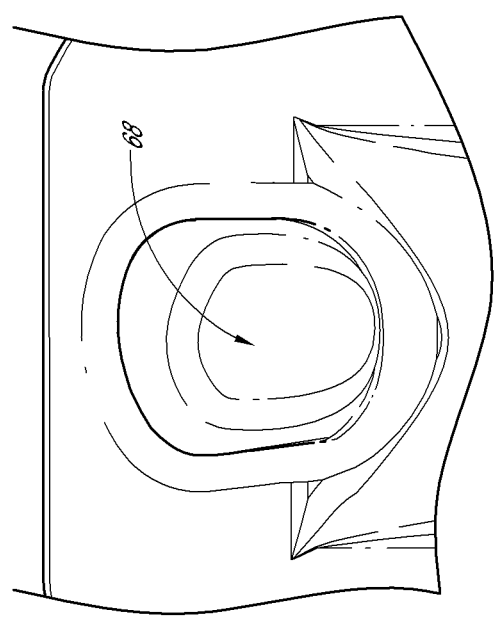
Figure 4A:
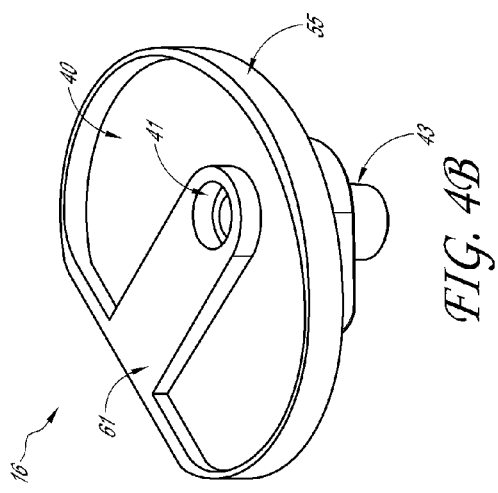
FIGS. 4A-4D are top, perspective, posterior and side views, respectively, of a tibial component of a knee prosthesis, according to one embodiment.
Figure 4B:
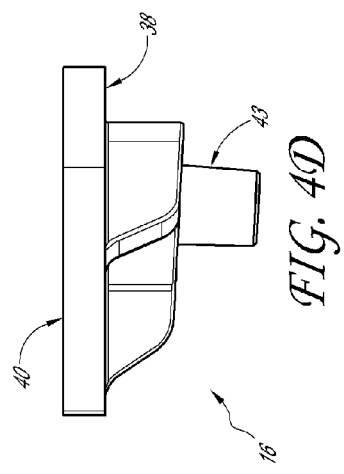
Figure 4C:
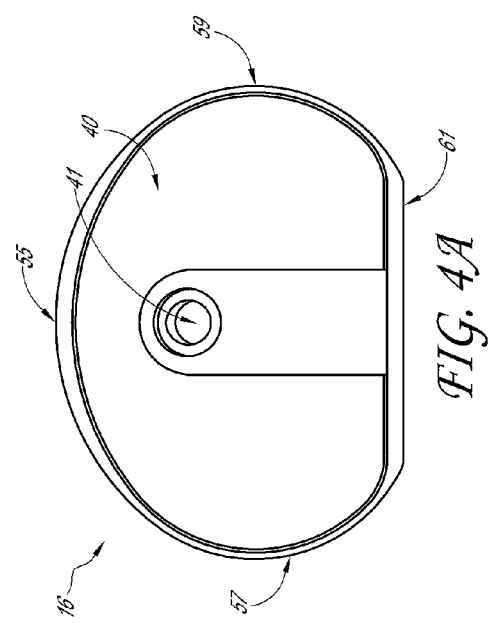
Figure 4D:
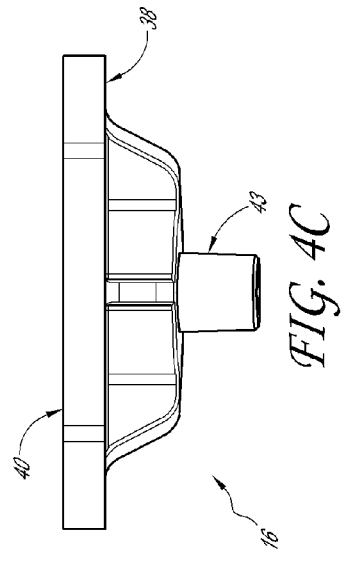

Turning now to FIGS. 3B, 3I and 3J, post 32 may also include a sloped anterior/superior surface 68 with a small, asymmetric concavity (or "cutout"). The concavity generally has a tapered posterior-to-anterior profile. As illustrated by FIG. 3J, the slope and especially the asymmetric concavity of anterior/superior surface 68 are configured to reduce contact with patellar component 18 as the knee moves into deep flexion. This reduced contact, in turn, reduces wear and tear on post 32 and patellar component 18.

Referring to FIGS. 3A, 3B and 3K, meniscal component 14 may also include an asymmetric anterior cutout 36 at the juncture of superior side 50 and anterior side 54. Cutout 36 is configured to minimize tenting of the patellar tendon over the meniscal component 14 as the knee flexes. Relief 36 also reduces the risk of patellar component 18 contacting the meniscal component 14 in situations in which the joint line has moved, either purposefully or as an unintended effect of the surgical procedure, proximally and anteriorly. As best seen in FIG. 3K, anterior/superior cutout 36 is positioned asymmetrically, closer to lateral side 56, to compensate for internal rotation of the tibia relative to the femur during flexion.

Referring to FIGS. 3C (medial side view), 3E (lateral side view), 3L (posterior view), 3M (medial cross-section), and 3N (lateral cross-section), meniscal component 14 may include yet another feature to enhance the kinematics of a knee in which knee prosthesis system 10 is implanted. FIG. 3L shows that the superior edge of posterior medial articulating surface 64a is higher than the superior edge of posterior lateral articulating surface 64b. In other words, posterior side 60 has a height H1 at the medial side that is greater than its height H2 at the lateral side. This is due to the fact that, in this embodiment, posterior medial articulating surface 64a has an upward slope or slant in an anterior-to-posterior direction, while posterior lateral articulation surface 64b has an approximately horizontal (or "flat") profile in an anterior-to-posterior direction. The difference between the two posterior articulating surfaces is best shown in FIGS. 3M (medial sloping surface 64a) and 3N (lateral horizontal surface 64b). These surfaces 64a, 64b are also shown in FIGS. 3C and 3E. In the embodiment shown, for example, the upward slope angle of medial articulating surface 64a is approximately 3 degrees, and the profile angle of the posterior articulating surface 64b is approximately 0 degrees. In alternative embodiments, slight changes to these angles may be made. For example, in one alternative embodiment, medial articulating surface 64a may have a slightly larger slope such as between about 4 degrees and about 5 degrees, and posterior articulating surface 64b may have a slight slope such as between about 1 degree and about 2 degrees. Thus, although the 3-degree/0-degree combination has been shown in tests to provide natural knee kinematics, other combinations might be possible. This configuration of medial articulating surface 64a and posterior articulating surface 64b is another feature that helps replicate natural knee kinematics in knee prosthesis 10 by helping keep medial condyle 25a of femoral component 12 in place while allowing lateral condyle 25b to translate posteriorly relative to meniscal component 14. Again, this facilitates tibial rotation and posterior translation during flexion.

Turning now to FIGS. 4A-4D, tibial component 16 according to one embodiment is shown in greater detail. In this embodiment, tibial component 16 generally includes a joint facing surface 40 for mating with meniscal component 14, a bone attachment surface 38, one or more attachment features 41 for attaching to meniscal component 14, and anterior 55, posterior 61, medial 57 and lateral 59 sides. Tibial component may also include a post 43 for extending into the tibia to enhance attachment to the bone. According to various embodiments, tibial component 16 may have any of a number of suitable sizes and shapes to attach to tibial bone and to meniscal component 14, and thus the embodiment shown is only one example. Tibial component may be made of any suitable material, typically but not necessarily metal or polymer.

Figure 5C:
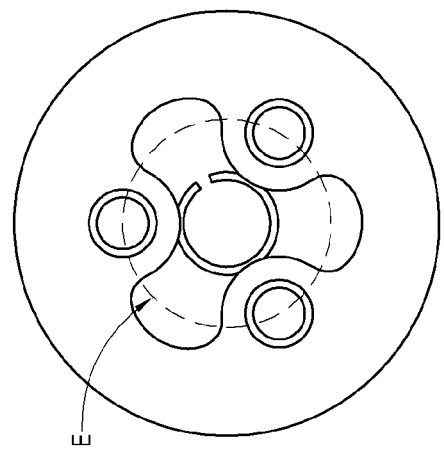
FIG. 5C is an anterior view of a prior art patellar component of a knee prosthesis.
Figure 5B:
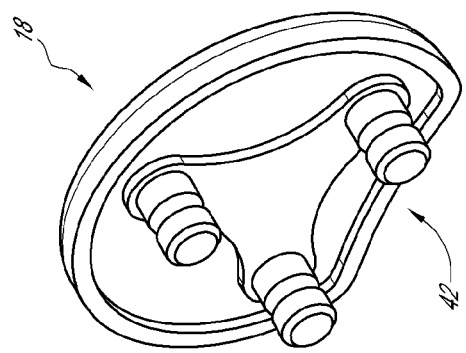
FIGS. 5A and 5B are anterior and perspective/posterior views, respectively, of a patellar component of a knee prosthesis, according to one embodiment.
Figure 5A:
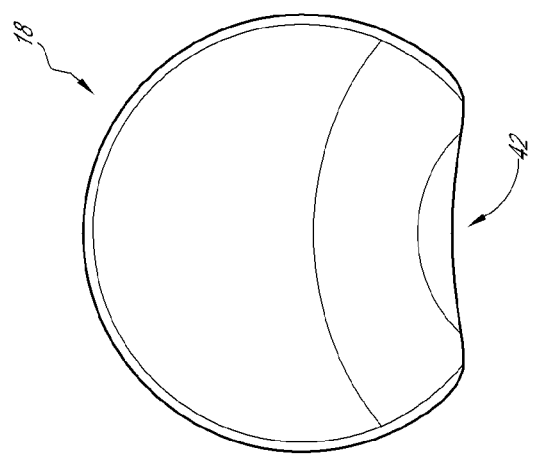
Figure 7A:
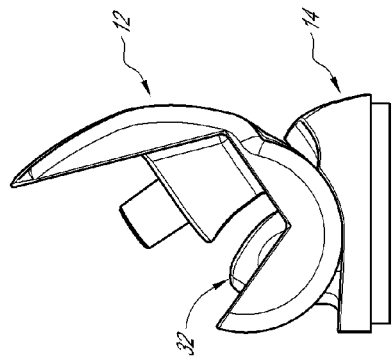
FIGS. 7A-7E are side views of the femoral and meniscal components through the same range of motion shown in FIGS. 6A-6E.
Figure 7B:
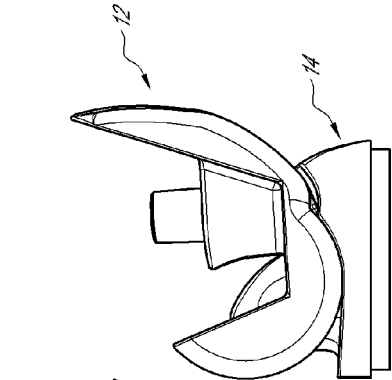
Figure 7C:
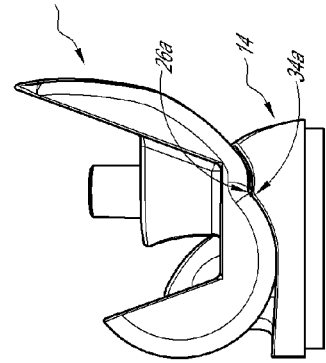
Figure 7D:
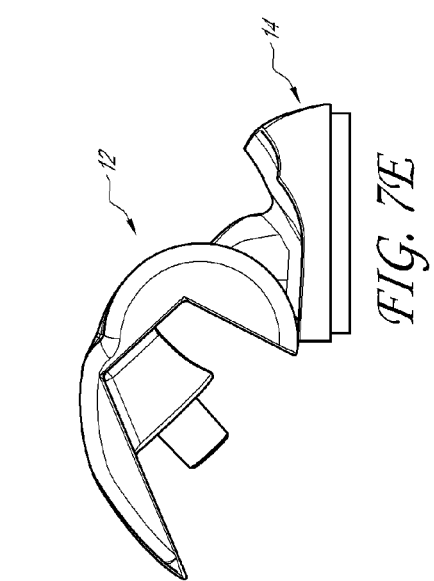
Figure 7E:
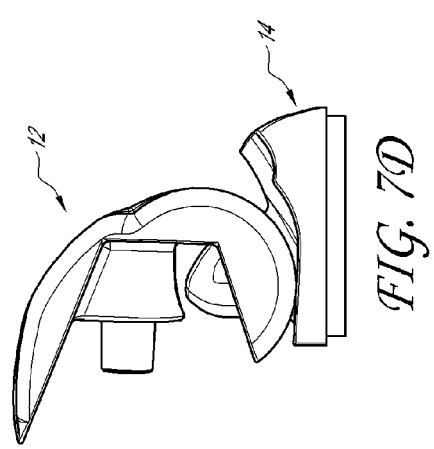
Figure 9C:
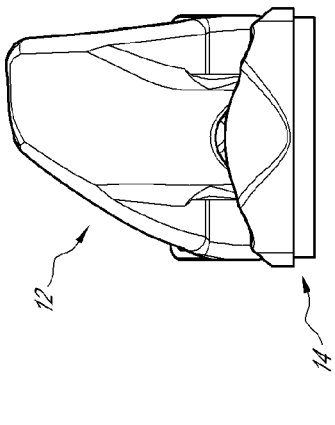
FIGS. 9A-9E are anterior views of the femoral and meniscal components through the same range of motion shown in FIGS. 6A-6E, 7A-7E and 8A-8E.
Figure 9B:
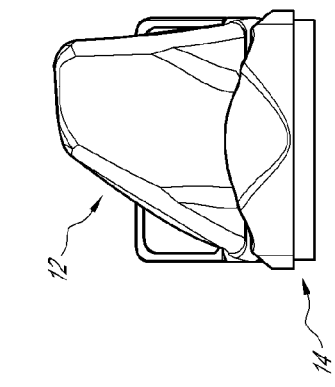
Figure 9A:
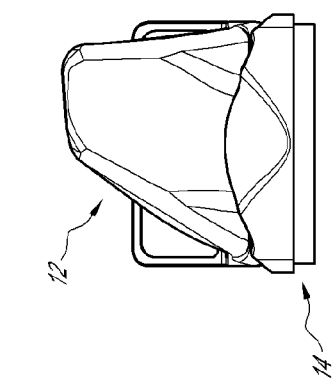
Figure 9E:
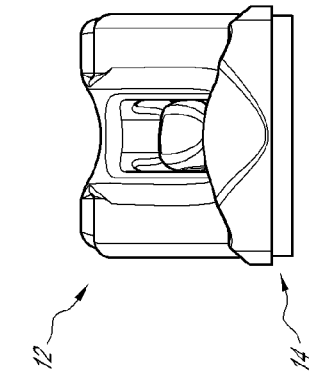
Figure 9D:
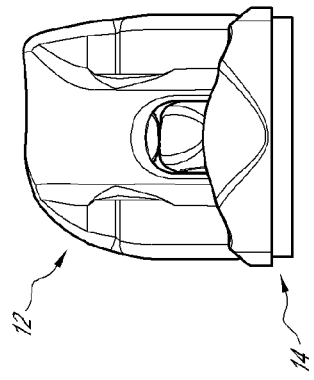

Referring now to FIGS. 5A and 5B, patellar component 18 is shown in greater detail. Patellar component 18 may have any suitable shape (domed, symmetric, asymmetric, etc.) and may include an inferior relief 42 (or "cutout"). In contrast, traditional patellar components have a circular anterior-view profile (FIG. 7C). Relief 42 reduces the risk of patellar component 18 contacting the meniscal component 14 during mid-to-deep flexion in situations (known as patella baja) in which the joint line has moved, either purposefully or as an unintended effect of the surgical procedure, proximally and anteriorly.

FIGS. 6-9 illustrate femoral component 12 and meniscal component 14 in various stages of motion of a knee through a range of motion from extension to flexion, to show how these two components 12, 14 interact with one another to facilitate natural knee kinematics. In each set of figures, the first figure (the "A" figure) shows components 12, 14 in 4 degrees of hyperextension, the second figure (the "B" figure) shows components 12, 14 in 0 degrees of flexion, the third figure (the "C" figure) shows components 12, 14 in 45 degrees of flexion, the fourth figure (the "D" Figure) shows components 12, 14 in 90 degrees of flexion, and the fifth figure (the "E" figure) shows components 12, 14 in 135 degrees of flexion. FIGS. 6A-6E are perspective views, FIGS. 7A-7E are medial side views, FIGS. 8A-8E are posterior views, and FIGS. 9A-9E are front views.

With the knee in 4 degrees of extension (i.e., maximal or hyper extension) (FIGS. 6A, 7A, 8A, 9A), protrusions 34a, 34b on meniscal component 14 mate with grooves 26a, 26b on femoral component 12 to provide stability to the joint by limiting rotation and anterior translation of femoral component 12 relative to meniscal component 14. Preventing such translation makes the patient's knee feel more stable and thus more natural. Additionally, the anterior side of protrusions 34a and 34b restricts posterior translation of the femoral component 12 relative to meniscal component 14, which prevents blunt impact and excessive forces and wear on the anterior cam surface 28a. Protrusions 34a, 34b may alternatively be referred to as a "wave." In alternative embodiments, protrusions 34a, 34b may be replaced with one protrusion that extends all the way across meniscal component 14 and/or grooves 26a, 26b may be replaced with one groove that extends all the way across femoral component 12.

Referring to FIGS. 6B, 7B, 8B and 9B, when the knee is in 0 degrees of flexion, protrusions 34a, 34b and grooves 26a, 26b still provide stability to the knee. At this point anterior cam surface 28a of intercondylar opening 28 contacts anterior surface 66a of post 32. This contact provides additional anterior-posterior stability and positions components 12, 14 relative to one another.

FIGS. 6C, 7C, 8C and 9C show components 12, 14 as if attached to a knee in 45 degrees of flexion. At this stage, which might be referred to as "mid-flexion," the tibia (and meniscal component 14) rotates internally relative to the femur (and femoral component 12). In other words, in the left knee (as in the figures), the tibia rotates clockwise in a top view relative to the femur as the knee flexes. In the right knee, the tibia rotates counterclockwise in top view in flexion. Also at this stage, posterior cam surface 28b of intercondylar opening 28 contacts posterior surface 66b of post 32. This contact begins to turn rotary motion of the two components 12, 14 into posterior translation of the lateral condyle 25b of femoral component 12 relative to meniscal component 14.

With the knee in 90 degrees of flexion, as in FIGS. 6D, 7D, 8D and 9D, posterior cam surface 28b slides down posterior surface 66b of post 32 and creates posterior translation and internal rotation of meniscal component 12 relative to femoral component 14. This rotation is illustrated well by FIG. 7D. Contact of posterior cam surface 28b with posterior surface 66b drives both condyles 25a, 25b in the posterior direction, but lateral condyle 25b translate posteriorly farther than medial condyle 25a.

In deep flexion (135 degrees), as in FIGS. 6E, 7E, 8E and 9E, the rotation of femoral component 12 relative to meniscal component 14 is even more pronounced. This is shown best in FIG. 7E. The reverse of these motions of components 12, 14 occurs when the knee is moved from flexion to extension.

What is claimed is:

1. A knee prosthesis for use in a total knee replacement surgical procedure, the knee prosthesis comprising:
    a femoral component comprising:
        a bone attachment side for attaching to a cut distal end of a femur;
        a joint facing side opposite the bone attachment side comprising:
            an anterior joint surface;
            a posterior joint surface having a cross-sectional shape defining a portion of a cylinder, wherein the posterior joint surface extends along at least 135 degrees of the cylinder and comprises:

a lateral condyle;
a medial condyle; and
an intercondylar opening disposed between the lateral and medial condyles; and
medial and lateral grooves extending across the femoral component between the anterior joint surface and the medial and lateral condyles;
a tibial component comprising:
a bone attachment side for attaching to a cut proximal end of a tibia; and
a joint facing side opposite the bone attachment side; and
a meniscal component, having an inferior side for mating with the tibial component, a superior side for mating with the femoral component, an anterior side, a posterior side, a lateral side and a medial side, the meniscal component further comprising:
an anterior articulating surface on the superior side for mating with the anterior joint surface of the femoral component;
a posterior lateral articulating surface on the superior side for mating with the lateral condyle of the femoral component, the posterior lateral articulating surface having an approximately horizontal profile in an anterior-to-posterior direction;
a posterior medial articulating surface on the superior side for mating with the medial condyle of the femoral component, the posterior medial articulating surface having an upward sloping profile in an anterior-to-posterior direction;
medial and lateral projections on the superior side for mating with the medial and lateral grooves of the femoral component;
a post extending from the superior surface and configured to mate with the intercondylar opening of the femoral component, wherein a central axis of the post is disposed closer to the posterior side than to the anterior side of the meniscal component; and
an anterior cutout on the anterior side of the superior surface to prevent injury to a patellar tendon.

2. A knee prosthesis as in claim 1, wherein the bone attachment side of the femoral component comprises three surfaces for attaching to a three-cut configuration of the distal end of the femur.

3. A knee prosthesis as in claim 1, wherein the bone attachment side of the femoral component comprises three surfaces for attaching to a five-cut configuration of the distal end of the femur.

4. A knee prosthesis as in claim 1, wherein the anterior joint surface of the femoral component includes a trochlear groove that is offset from a midline axis of the femoral component in a direction slanting from medial to lateral as the groove extends toward an anterior, superior edge of the femoral component.

5. A knee prosthesis as in claim 1, wherein the post of the meniscal component has an asymmetrical shape in at least two dimensions.

6. A knee prosthesis as in claim 5, wherein a posterior aspect of the post has a helical twist shape as viewed from a superior aspect.

7. A knee prosthesis as in claim 5, wherein an anterior convex surface of the post conforms to an anterior concave surface of the intercondylar opening of the femoral component, and wherein a posterior convex surface of the post confirms to a posterior concave surface of the intercondylar opening of the femoral component.

8. A knee prosthesis as in claim 5, wherein a posterior portion of the post is wider than an anterior portion of the post.

9. A knee prosthesis as in claim 5, wherein a superior surface of the post slopes downward in a posterior-to-anterior direction, and wherein the superior surface has an asymmetric convex configuration.

10. A knee prosthesis as in claim 1, wherein the anterior cutout on the meniscal component is asymmetrically disposed along the anterior side, biased toward the lateral side.

11. A knee prosthesis as in claim 1, further including a patellar component having a cutout portion on an inferior edge.

12. A meniscal component of a knee prosthesis for use in a total knee replacement surgical procedure, the meniscal component comprising:
an inferior side for mating with a tibial component of a knee prosthesis;
a superior side for mating with a femoral component of the knee prosthesis;
an anterior side, a posterior side, a lateral side and a medial side;
a concave anterior articulating surface on the superior side toward the anterior side for mating with a convex anterior joint surface of a femoral component;
a posterior lateral articulating surface on the superior side for mating with a lateral condyle of the femoral component, the posterior lateral articulating surface having an approximately horizontal profile in an anterior-to-posterior direction;
a posterior medial articulating surface on the superior side for mating with a medial condyle of the femoral component, the posterior medial articulating surface having an upward sloping profile in an anterior-to-posterior direction;
medial and lateral projections on the superior side for mating with medial and lateral grooves on the femoral component;
a post extending from the superior surface and configured to mate with the intercondylar opening of the femoral component, wherein a central axis of the post is disposed closer to the posterior side than to the anterior side of the meniscal component; and
an anterior cutout on the anterior side of the superior surface to prevent injury to the patellar tendon.

13. A meniscal component as in claim 12, wherein the post of the meniscal component has an asymmetrical shape in at least two dimensions.

14. A meniscal component as in claim 13, wherein the post of the meniscal component has a helical twist shape as viewed from a superior aspect.

15. A meniscal component as in claim 13, wherein an anterior convex surface of the post confirms to an anterior concave surface of the intercondylar opening of the femoral component, and wherein a posterior convex surface of the post conforms to a posterior concave surface of the intercondylar opening of the femoral component.

16. A meniscal component as in claim 13, wherein a posterior portion of the post is wider than an anterior portion of the post.

17. A meniscal component as in claim 13, wherein the superior surface of the post slopes downward in a posterior-to-anterior direction, and wherein the superior surface has an asymmetric convex configuration.

18. A knee prosthesis for use in a total knee replacement surgical procedure, the knee prosthesis comprising:
a femoral component comprising:
a bone attachment side for attaching to a cut distal end of a femur;
a joint facing side opposite the hone attachment side comprising:
an anterior joint surface;
a posterior joint surface having a cross-sectional shape defining a portion of a cylinder, wherein the posterior joint surface extends along at least 135 degrees of the cylinder and comprises:
a lateral condyle;
a medial condyle; and
an intercondylar opening disposed between the lateral and condyles; and
medial and lateral grooves extending across the femoral component between the anterior joint surface and the medial and lateral condyles; and
a meniscal component, having a bone attachment side for attaching to a cut proximal end of a tibia, a superior side for mating with the femoral component, an anterior side, a posterior side, a lateral side and a medial side, the meniscal component further comprising:
an anterior articulating surface on the superior side for mating with the anterior joint surface of the femoral component;
a posterior lateral articulating surface on the superior side for mating with the lateral condyle of the femoral component, the posterior lateral articulating surface having an approximately horizontal profile in an anterior-to-posterior direction;
a posterior medial articulating surface on the superior side for mating with the medial condyle of the femoral component, the posterior medial articulating surface having an upward sloping profile in an anterior-to-posterior direction;
medial and lateral projections on the superior side for mating with the medial and lateral grooves of the femoral component;
a post extending from the superior surface and configured to mate with the intercondylar opening of the femoral component, wherein a central axis of the post is disposed closer to the posterior side than to the anterior side of the meniscal component; and
an anterior cutout on the anterior side of the superior surface to prevent injury to a patellar tendon.

19. A knee prosthesis as in claim 18, further comprising a patellar component having a cutout portion on an inferior edge.

* * * * *

UNITED STATES PATENT AND TRADEMARK OFFICE
CERTIFICATE OF CORRECTION

PATENT NO.        : 8,409,293 B1
APPLICATION NO.   : 13/281748
DATED             : April 2, 2013
INVENTOR(S)       : Michael J. Howard and Kenneth D. Johannaber Page 1 of 1

It is certified that error appears in the above-identified patent and that said Letters Patent is hereby corrected as shown below:

In the Claims

At col 13, line 50 (claim 3, line 2),
  "comprises three surfaces"

should read:
  -- comprises five surfaces --

Signed and Sealed this
Thirteenth Day of January, 2015

Michelle K. Lee
*Deputy Director of the United States Patent and Trademark Office*